United States Patent [19]

Stähle et al.

[11] 4,259,346
[45] Mar. 31, 1981

[54] BRADYCARDIAC PHARMACEUTICAL COMPOSITIONS AND METHOD OF USE

[75] Inventors: Helmut Stähle; Herbert Köppe; Werner Kummer, all of Ingelheim am Rhein, Fed. Rep. of Germany; Walter Kobinger, Vienna, Australia; Christian Lillie, Vienna, Australia; Ludwig Pichler, Vienna, Australia; Wolfgang Hoefke, Budenheim; Wolfram Gaida, Ingelheim am Rhein, both of Fed. Rep. of Germany

[73] Assignee: Boehringer Ingelheim GmbH, Ingelheim am Rhein, Fed. Rep. of Germany

[21] Appl. No.: 103,584

[22] Filed: Dec. 14, 1979

[30] Foreign Application Priority Data

Dec. 21, 1978 [DE] Fed. Rep. of Germany ....... 2855306

[51] Int. Cl.³ ........................................... A61K 31/415
[52] U.S. Cl. .............................................. 424/273 R
[58] Field of Search ................................... 424/273 R

[56] References Cited

U.S. PATENT DOCUMENTS

| | | | |
|---|---|---|---|
| 3,462,433 | 8/1969 | Stahle et al. | 424/273 |
| 3,969,525 | 7/1976 | Wolf | 424/273 |
| 4,100,292 | 7/1978 | Stahle et al. | 424/273 |

FOREIGN PATENT DOCUMENTS 2457979 6/1976 Fed. Rep. of Germany ...... 424/273 R

Primary Examiner—Frederick E. Waddell
Attorney, Agent, or Firm—Hammond & Littell, Weissenberger & Muserlian

[57] ABSTRACT

Pharmaceutical compositions containing as an active ingredient a compound of the formula

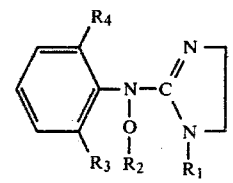

wherein
$R_1$ is hydrogen or lower alkyl,
$R_2$ is hydrogen, lower alkyl, hydroxy-lower alkyl, chloro-hydroxy-propyl, 2,3-epoxy-propyl, alkoxy-alkyl, aminoalkyl, N-substituted aminoalkyl, benzyl or phenethyl,
$R_3$ is hydrogen or halogen, and
$R_4$ is halogen or methyl, or a non-toxic, pharmacologically acceptable acid addition salt thereof; and a method of using the same as bradycardiacs.

1 Claim, No Drawings

BRADYCARDIAC PHARMACEUTICAL COMPOSITIONS AND METHOD OF USE

This invention relates to novel bradycardiac pharmaceutical compositions containing a 2-N-aryl-hydroxyamino-2-imidazoline as the active ingredient, as well as to a method of using the same for slowing the heart rate.

THE PRIOR ART

German Offenlegungsschrift No. 2,457,979 discloses certain 2-N-aryl-hydroxyamino-2-imidazolines of the formula

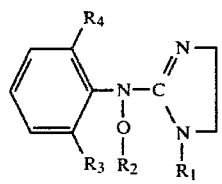

(I)

wherein
- $R_1$ is hydrogen or lower alkyl,
- $R_2$ is hydrogen, lower alkyl, hydroxy-lower alkyl, chloro-hydroxy-propyl, 2,3-epoxy-propyl, alkoxyalkyl, aminoalkyl, N-substituted aminoalkyl, benzyl or phenethyl,
- $R_3$ is hydrogen or halogen, and
- $R_4$ is halogen or methyl, and non-toxic, pharmacologically acceptable acid addition salts thereof.

The German publication further discloses that the compounds exhibit hypotensive activity and are therefore useful for the treatment of hypertension.

THE INVENTION

We have discovered that the compounds disclosed in the German publication, that is, those embraced by formula I above and their non-toxic, pharmacologically acceptable acid addition salts, also possess bradycardiac properties.

More particularly, the present invention relates to pharmaceutical dosage unit compositions containing as an active ingredient a compound of the formula I above or a non-toxic, pharmacologically acceptable acid addition salt thereof, as well as to a method of using the same as bradycardiacs.

The bradycardiac activity of the compounds was ascertained in anesthetized cats and rats, as well as in spinal rats.

For instance, after intravenous administration of 0.3 and 1.0 mgm/kg, respectively, of 2-[N-(2,6-dichlorophenyl)-methoxyamino]-2-imidazoline to anesthetized cats, a distinct dose-dependent bradycardia was observed.

Intravenous administration of 0.6 mgm/kg of the same compound to anesthetized rats first produced an increase in the blood pressure by 5 mm Hg and then a decrease by 15 mm Hg; simultaneously, it produced a decrease in the heart rate by 58 beats per minute. At a dose of 2.5 mgm/kg the blood pressure first increased by 22 mm Hg and then decreased by 39 mm Hg while the heart rate decreased by 145 beats per minute.

After elimination of the central nervous system, 2-[N-(2,6-dichloro-phenyl)-methoxyamino]-2-imidazoline showed only bradycardiac activity in the rat. Thus, in the spinal rat 0.6 mgm/kg of the compound produced a decrease in the heart rate by 70 beats per minute, and 2.5 mgm/kg produced a decrease in the heart rate by 140 beats per minute, which indicates a direct action on the heart. These results clearly distinguish this particular compound from other bradycardiac-active compounds, such as clonidine, calcium antagonists of the verapamil type, cholinergic compounds and $\beta$-adrenergic receptor blockers.

The remaining compounds embraced by formula I and their non-toxic, pharmacologically acceptable acid addition salts exhibit the same activity. The following table shows the doses of various representative species of the genus which produce a decrease in the heart rate by 150 beats per minute (D 150-values) in the spinal rat.

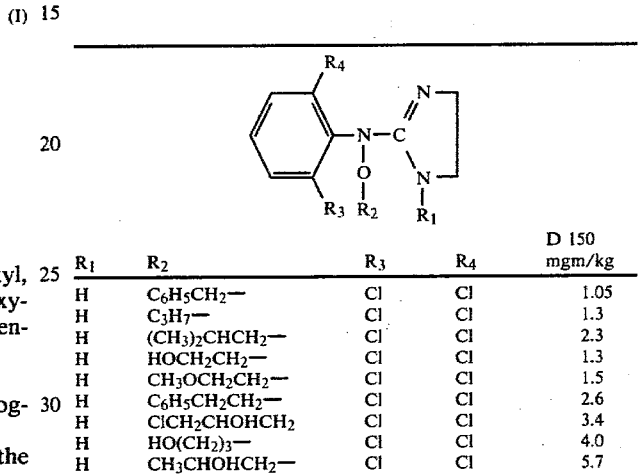

| $R_1$ | $R_2$ | $R_3$ | $R_4$ | D 150 mgm/kg |
|---|---|---|---|---|
| H | $C_6H_5CH_2$— | Cl | Cl | 1.05 |
| H | $C_3H_7$— | Cl | Cl | 1.3 |
| H | $(CH_3)_2CHCH_2$— | Cl | Cl | 2.3 |
| H | $HOCH_2CH_2$— | Cl | Cl | 1.3 |
| H | $CH_3OCH_2CH_2$— | Cl | Cl | 1.5 |
| H | $C_6H_5CH_2CH_2$— | Cl | Cl | 2.6 |
| H | $ClCH_2CHOHCH_2$ | Cl | Cl | 3.4 |
| H | $HO(CH_2)_3$— | Cl | Cl | 4.0 |
| H | $CH_3CHOHCH_2$— | Cl | Cl | 5.7 |

For pharmaceutical purposes the compounds of the formula I or their non-toxic, pharmacologically acceptable acid addition salts are administered to warm-blooded animals perorally, parenterally or rectally as active ingredients in customary dosage unit compositions, that is, compositions in dosage unit form consisting essentially of an inert pharmaceutical carrier and one effective brady-cardiac dosage unit of the active ingredient, such as tablets, coated pills, capsules, wafers, powders, solutions, suspensions, emulsions, syrups, suppositories and the like. One effective bradycardiac dosage unit of the compounds of the formula I or their non-toxic, pharmacologically acceptable acid addition salts is from 0.083 to 1.67 mgm/kg body weight, preferably 0.166 to 0.83 mgm/kg body weight.

The following examples illustrate a few bradycardiac pharmaceutical dosage unit compositions comprising a compound of the formula I or a non-toxic, pharmacologically acceptable acid addition salt thereof as an active ingredient and represent the best modes contemplated of putting the invention into practical use. The parts are parts by weight unless otherwise specified.

EXAMPLE 1

Tablets

The tablet composition is compounded from the following ingredients:

| | |
|---|---|
| 2-[N-(2,6-Dichloro-phenyl)-methoxyamino]-2-imidazoline | 50.0 parts |
| Lactose | 95.0 parts |
| Corn starch | 45.0 parts |
| Colloidal silicic acid | 2.0 parts |
| Soluble starch | 5.0 parts |

-continued

| | |
|---|---|
| Magnesium stearate | 3.0 parts |
| Total | 200.0 parts |

Preparation

The active ingredient is admixed with a substantial portion of each of the excipients, and the mixture is granulated with the aid of an aqueous solution of the soluble starch. The resulting granulate is dried and admixed with the remainder of the excipients, and the composition is compressed into 200 mgm-tablets in a conventional tablet making machine. Each tablet is an oral bradycardiac dosage unit composition containing 50 mgm of the active ingredient.

EXAMPLE 2

Coated pills

The pill core composition is compounded from the following ingredients.

| | |
|---|---|
| 2-[N-(2,6-Dichloro-phenyl)-methoxyamino]-2-imidazoline hydrochloride | 20.0 parts |
| Lactose | 100.0 parts |
| Colloidal silicic acid | 2.0 parts |
| Corn starch | 65.0 parts |
| Soluble starch | 5.0 parts |
| Magnesium stearate | 3.0 parts |
| Total | 195.0 parts |

Preparation

The ingredients are compounded in the same manner as in Example 1, and the composition is compressed into 195 mgm-pill cores which are subsequently coated in conventional manner with a thin shell consisting essentially of a mixture of sugar, talcum and gum arabic. Each coated pill is an oral bradycardiac dosage unit composition containing 20 mgm of the active ingredient.

EXAMPLE 3

Rectal suppositories

The suppository composition is compounded from the following ingredients:

| | |
|---|---|
| 2-[N-(2,6-Dichloro-phenyl)-methoxyamino]-2-imidazoline | 50.0 parts |
| Lactose | 250 parts |
| Suppository base (e.g. cocoa butter) | 1400.0 parts |
| Total | 1700.0 parts |

Preparation

The active ingredient and the lactose are intimately admixed with each other, the mixture is homogeneously blended into the molten suppository base, and 1700 mgm-portions of the resulting compositions are poured into cooled suppository molds and allowed to harden therein. Each suppository is a bradycardiac rectal dosage unit composition containing 50 mgm of the active ingredient.

EXAMPLE 4

Hypodermic solution

The solution is compounded from the following ingredients:

| | |
|---|---|
| 2-[N-(2,6-Dichloro-phenyl)-methoxyamino]-2-imidazoline | 20.0 parts |
| Sodium chloride | 5.0 parts |
| Double-distilled water q.s.ad | 2000.0 parts by vol. |

Preparation

The active ingredient is dissolved in a sufficient amount of double-distilled water, the solution is diluted with double-distilled water to the indicated volume, and the solution is filtered until free from suspended particles. The filtrate is filled under aseptic conditions into 2 cc-ampules which are then sterilized and sealed. The contents of each ampule are an injectable bradycardiac composition containing 20 mgm of the active ingredient.

EXAMPLE 5

Drop solution

The solution is compounded from the following ingredients:

| | |
|---|---|
| 2-[N-(2,6-Dichloro-phenyl)-methoxyamino]-2-imidazoline | 0.70 parts |
| Methyl-p-hydroxy-benzoate | 0.07 parts |
| Propyl p-hydroxy-benzoate | 0.03 parts |
| De-mineralized water q.s.ad | 100.00 parts by vol. |

Preparation

The active ingredient and the p-hydroxy-benzoates are dissolved in the de-mineralized water, the solution is filtered, and the filtrate is filled into 100 ml-bottles equipped with a dropping spout. 5 ml of the solution are a bradycardiac oral dosage unit composition containing 35 mgm of the active ingredient.

Any one of the other compounds embraced by formula I or a non-toxic, pharmacologically acceptable acid addition salt thereof may be substituted for the particular active ingredient in Examples 1 through 5. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of lowering the heart rate in a warm-blooded animal in need thereof, which comprises perorally, parenterally or rectally administering to said animal an effective bradycardiac amount of a compound of the formula

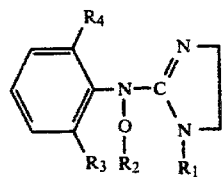
wherein
R₁ is hydrogen or lower alkyl,
R₂ is hydrogen, lower alkyl, hydroxy-lower alkyl, chloro-hydroxy-propyl, 2,3-epoxy-propyl, alkoxy-alkyl, aminoalkyl, N-substituted aminoalkyl, benzyl or phenethyl,
R₃ is hydrogen or halogen, and
R₄ is halogen or methyl, or a non-toxic, pharmacologically acceptable acid addition salt thereof.
* * * * *